US008616764B2

(12) United States Patent
Ladru et al.

(10) Patent No.: US 8,616,764 B2
(45) Date of Patent: Dec. 31, 2013

(54) METHOD FOR TESTING A THERMOGRAPHY APPARATUS, DESIGNED FOR CARRYING OUT A THERMOGRAPHY METHOD, FOR ITS CORRECT OPERATION, TEST COMPONENT THEREFOR AND METHOD FOR ITS PRODUCTION

(75) Inventors: Francis-Jurjen Ladru, Berlin (DE); Bernhard Siebert, Berlin (DE)

(73) Assignee: Siemens Aktiengesellschaft, München (DE)

( * ) Notice: Subject to any disclaimer, the term of this patent is extended or adjusted under 35 U.S.C. 154(b) by 101 days.

(21) Appl. No.: 13/231,148

(22) Filed: Sep. 13, 2011

(65) Prior Publication Data

US 2012/0069865 A1 Mar. 22, 2012

(30) Foreign Application Priority Data

Sep. 17, 2010 (EP) .................................... 10177354

(51) Int. Cl.
*G01K 15/00* (2006.01)
*C23C 2/38* (2006.01)

(52) U.S. Cl.
USPC ............................................ 374/1; 427/357

(58) Field of Classification Search
USPC ................... 427/357, 435, 8; 374/1
See application file for complete search history.

(56) References Cited

U.S. PATENT DOCUMENTS 5,562,345 A * 10/1996 Heyman et al. ................... 374/5
6,024,792 A    2/2000 Kurz et al.
6,383,570 B1 *  5/2002 Bose et al. ..................... 427/405
7,005,015 B2 *  2/2006 Burgel et al. .................. 148/428
7,176,528 B2 *  2/2007 Couillard et al. .............. 257/347
7,303,374 B2 * 12/2007 Li et al. ............................ 416/61
2005/0214564 A1  9/2005 Subramanian
2008/0124468 A1  5/2008 Kang

FOREIGN PATENT DOCUMENTS

DE    102008011249 A1  9/2009
EP       0412397 B1    2/1991
EP       0486489 B1    5/1992
EP       0786017 B1    7/1997

(Continued)

OTHER PUBLICATIONS

Fengling Yu and Ted D. Bennetta, "Phase of thermal emission spectroscopy for properties measurements of delaminating thermal barrier coatings", Journal of Applied Physics 98, 103501, pp. 1-8, 2005.*

(Continued)

*Primary Examiner* — Lisa Caputo
*Assistant Examiner* — Nasir U Ahmed (57) ABSTRACT

A test component coated with a coating system is provided. In at least one defined region of the test component, there is a delamination having defined properties deliberately introduced into the coating system. The test component may be employed in a method for testing a thermography apparatus that is designed for carrying out a thermography method, for its correct operation with a view to the detection of delaminations. In order to test the thermography apparatus, the at least one defined delamination of the coating system is detected on the test component by using the thermography method employed in the thermography apparatus.

10 Claims, 6 Drawing Sheets

(56) References Cited

FOREIGN PATENT DOCUMENTS

| | | |
|---|---|---|
| EP | 0892090 A1 | 1/1999 |
| EP | 1204776 B1 | 5/2002 |
| EP | 1306454 B1 | 5/2003 |
| EP | 1319729 A1 | 6/2003 |
| EP | 1750123 A2 | 2/2007 |
| EP | 1916517 A1 | 4/2008 |
| WO | WO 99/67435 | 12/1999 |
| WO | WO 00/44949 | 8/2000 |

OTHER PUBLICATIONS

A. Portinhaa, V. Teixeiraa, J. Carneiroa, J. Martinsb, M.F. Costac, R. Vassend, D. Stoeverd, "Characterization of thermal barrier coatings with a gradient in porosity", Surface & Coatings Technology 195 (2005), pp. 245-251.*

YongQing Wang ., G. Sayrej, "Commercial thermal barrier coatings with a double-layer bond coat on turbine vanes and the process repeatability", Surface & Coatings Technology 203 (2009), pp. 2186-2192.*

* cited by examiner

METHOD FOR TESTING A THERMOGRAPHY APPARATUS, DESIGNED FOR CARRYING OUT A THERMOGRAPHY METHOD, FOR ITS CORRECT OPERATION, TEST COMPONENT THEREFOR AND METHOD FOR ITS PRODUCTION

CROSS REFERENCE TO RELATED APPLICATIONS

This application claims priority of European Patent Office application No. 10177354.7 EP filed Sep. 17, 2010, which is incorporated by reference herein in its entirety.

FIELD OF INVENTION

The present invention relates to a method for testing a thermography apparatus, designed for carrying out a thermography method, for its correct operation. The invention furthermore relates to a test component, which is used in the test method, and to a method for producing such a test component.

BACKGROUND OF INVENTION

Components which are exposed to high thermal stresses during their use, for instance turbine guide vanes or rotor blades (both referred to below as turbine blades for brevity), are generally made of refractory nickel- or cobalt-based alloys. Although such alloys have a high thermal load-bearing capacity, the components generally also need to be provided with a corrosion- and/or oxidation-inhibiting layer in order to extend their lifetime during the conditions prevailing during operation. In addition, a thermal barrier coating is generally also employed, which is applied onto the oxidation- and/or corrosion-inhibiting layer in order to reduce the temperature which this layer experiences and thus further extend the lifetime of the component. In this case, good bonding of the layer in question onto the underlying substrate is of great importance, since local disbonding of the layer increases the risk of flaking, so that the underlying substrate material is directly exposed to the thermally highly stressful ambient conditions, which necessitates premature replacement of the corresponding component. Highly stressed coated components such as turbine blades are therefore examined for qualification of the coating by means of random sampling or examined alongside manufacture to one hundred percent nondestructively by means of thermography in order to ensure defect-free bonding of the coating.

SUMMARY OF INVENTION

To this end, thermography apparatuses are used in which the delaminations, i.e. layer disbonding, are detected by means of a thermography method. The thermography apparatuses are checked from time to time for their correct operation and for calibration, in order to ensure that delaminations can be detected reliably by the thermography methods.

It is an object of the present invention to provide a test method with which a thermography apparatus can be tested reliably for its capacity to detect delaminations. It is another object of the present invention to provide a test component which allows reliable testing of a thermography apparatus for its capacity to detect delaminations. Lastly, it is an object of the present invention to provide a method for producing such a test component.

These objects are respectively achieved by the features of the independent claims. The dependent claims contain advantageous configurations of the invention.

In the method according to the invention for producing a test component, which has a surface coated with a coating system, at least one region which comprises a defined delamination of the coating system, i.e. defined layer disbonding, is deliberately produced on the surface. The test component may in particular be configured as a turbine blade, i.e. as a guide vane or rotor blade of a turbine.

With a test component, which comprises one or more known sites with defined layer disbonding, a thermography apparatus designed for detecting such delaminations by means of thermography methods can be tested reliably for whether the defined delaminations can be detected sufficiently accurately by means of the thermography method. By the deliberate production of delaminations, their size and the degree of residual adhesion of the coating on the underlying substrate material can be adjusted in a defined way. Further parameters, which can be adjusted in a defined way with the method according to the invention for producing a test component, are the position of the delamination on the component and its geometrical shape. In particular, components which comprise a plurality of defined delaminations that differ at least by one of the features: position, size, shape or residual adhesion on the underlying substrate, can also be produced by the method. In this way, the test component thus produced can be used to test the thermography apparatus over a full range of delaminations having different properties.

The production of the defined delamination may in particular comprise the steps:

covering an uncoated region, at least one defined region of the surface of the component remaining uncovered;
applying an auxiliary layer onto the at least one uncovered region of the surface, the auxiliary layer being selected so that the coating system has a lower adhesion compared with the surface of the component itself;
removing the covering;
coating the component with the coating system.

In this case, a solid or liquid material may be used as the auxiliary layer.

By using masks comprising openings of defined shape and size for covering the turbine component, auxiliary layers with a defined size and shape can thus be produced. Furthermore, when producing the auxiliary layers, it is also possible to generate different layer thicknesses which influence the degree of residual adhesion of the delaminated coating system on the auxiliary layer.

Both thermal spraying methods such as high velocity flame spraying (HVOF, high velocity oxygen fuel), cold gas spraying or plasma spraying, in particular atmospheric plasma spraying (APS), and physical vapor deposition methods, such as electron beam physical vapor deposition (EB-PVD), may in principle be used for producing auxiliary layers. Particularly with atmospheric plasma spraying as a thermal spraying method, the auxiliary layers can be produced economically and with sufficient precision. By suitable selection of the method parameters in the chosen methods for applying the auxiliary layer, it is possible to adjust the surface roughness of the auxiliary layer in such a way that different roughnesses can be generated by the same method, so that the residual adhesion of the coating system can be influenced.

A ceramic layer may in particular be employed as the auxiliary layer, for example a layer of zirconium oxide which is at least partially stabilized in its lattice structure with yttrium oxide (YSZ, yttria-stabilized zirconia). Nevertheless, other materials may also be used for forming the auxiliary layer so long as the coating system adheres less well on the material of the auxiliary layer than on the substrate material of the component, or the auxiliary layer has a different thermal conductivity. The residual adhesion of the coating system may in this case be influenced by the material selection for the auxiliary layer.

The auxiliary layer should have a thickness of at least 10 µm, in order to induce the delaminations sufficiently reliably. In general, layer thicknesses in the range of between 10 and 100 µm are suitable, particularly in the range of between 10 and 50 µm, preferably between 30 and 40 µm. Layer thicknesses of more than 100 µm are nevertheless also possible in principle.

The coating system, with which the test component is coated, preferably comprises at least one bond coat which furthermore has an oxidation- and/or corrosion-inhibiting effect, for instance a so-called MCrAlY layer, where M stands for iron (Fe), cobalt (Co) or nickel (Ni) and Y stands for a rare earth element, in particular yttrium and/or hafnium. As an alternative or in addition, the coating system comprises a thermal barrier coating (TBC) which may be formed in particular as a zirconium oxide layer at least partially stabilized in its structure with yttrium oxide (YSZ).

Advantageous test components can be produced by the method according to the invention for producing a test component. In particular, any desired number of defects, of which the size, shape and intensity of the delamination can furthermore be adjusted in a controlled way, can be introduced into the test component at any desired position. The production of the deliberate delaminations can also be carried out on any component type and with any coating. Lastly, fewer components need to be reserved for examinations/tests than in the prior art, in which, for testing a thermography apparatus, operation is typically carried out with blades which have suffered from an adhesion deficit owing to the preceding processes, but without the adhesion deficit having been deliberately introduced. In this case, there is usually only one delamination at a single position with an as yet unknown size and intensity of the delamination, which reduces the reliability during the testing or first necessitates determination of the delamination with a thermography apparatus which is known to function correctly. Furthermore, the blades used in the prior art are taken from the production process at a relatively late stage, so that unnecessary costs are incurred. In contrast to this, in the scope of the method according to the invention for producing a test component it is possible to use a component which drops out of the production chain early and would therefore have been classified early on as a reject component. As such, it no longer represents any significant value and, if it was not used as a test component, would be sent for scrap. Overall, the production costs and the subsequent test unreliability when testing the thermography apparatus are reduced when producing a test component by the method according to the invention.

The invention furthermore provides a test component coated with a coating system. In at least one defined region, the test component comprises a deliberately introduced delamination with defined properties in the coating system. Here, in particular, defined properties are intended to mean the position, size and shape of the delamination, as well as the degree of disbonding.

With the component according to the invention, which may be configured in particular as a turbine blade, a thermography apparatus in which delaminations are intended to be detected by a thermography method can be tested precisely for its correct operation since, owing to the defined properties of the delaminations in the test component, thermography signals can be recorded and evaluated for different degrees of delamination, positions, sizes and shapes. In the prior art, a plurality of turbine blades have generally been necessary for this, the delaminations of which had furthermore not been specified sufficiently before the testing so that only less accurate results have been possible in comparison with the test component according to the invention.

In the at least one region of the test component comprising the deliberately introduced delamination, there may be an auxiliary layer between the surface of the component and the coating system, which has a lower adhesion to the coating system or a different thermal conductivity than the surface of the component. As such an auxiliary layer, it is for example possible to provide a ceramic layer, for instance a layer of zirconium oxide which is at least partially stabilized with yttrium oxide (YSZ). The thickness of the auxiliary layer is preferably at least 10 µm and may lie in the range of between 10 µm and 100 µm, preferably in the range of between 10 and 50 µm, particularly in the range of between 30 and 40 µm, although greater layer thicknesses are also possible in principle.

The use of an auxiliary layer greatly assists controlled production of the delamination. The size and shape of the delamination can then be influenced by the size and shape of the auxiliary layer, and the degree of delamination by the thickness, roughness and material of the auxiliary layer.

The test component may in particular have a coating system which comprises at least one bond coat that furthermore has oxidation- and/or corrosion-inhibiting properties, for instance an MCrAlY layer, and/or at least one thermal barrier coating, for example a zirconium oxide layer at least partially stabilized in its structure with yttrium oxide (YSZ). Such coating systems are employed in particular for turbine blades, so that a test component having such a coating is suitable in particular for testing thermography apparatuses which are used to detect delaminations in turbine components. In principle, however, the test component may also have different coating systems which are selected specially with a view to the coating systems, in which delaminations are intended to be detected in the thermography apparatus.

The invention furthermore provides a method for testing a thermography apparatus, designed for carrying out a thermography method, for its correct operation with a view to the detection of delaminations. In the method, in order to test the thermography apparatus for its correct operation, a test component according to the invention is employed, which may in particular be configured as a turbine blade. With the test component, the at least one defined delamination of the coating system is detected by means of the thermography method employed in the thermography apparatus. As has already been explained with reference to the test component itself, or the method for producing such a test component, the use of the test component offers the advantage that a wide range of different delaminations can be tested by means of a single test component, and that the accuracy of the test method is increased compared with the prior art since the properties of the delamination are already known sufficiently accurately before the test.

BRIEF DESCRIPTION OF THE DRAWINGS

Other features, properties and advantages of the present invention may be found in the following description of exemplary embodiments with reference to the appended figures.

DETAILED DESCRIPTION OF INVENTION

Figure 1:
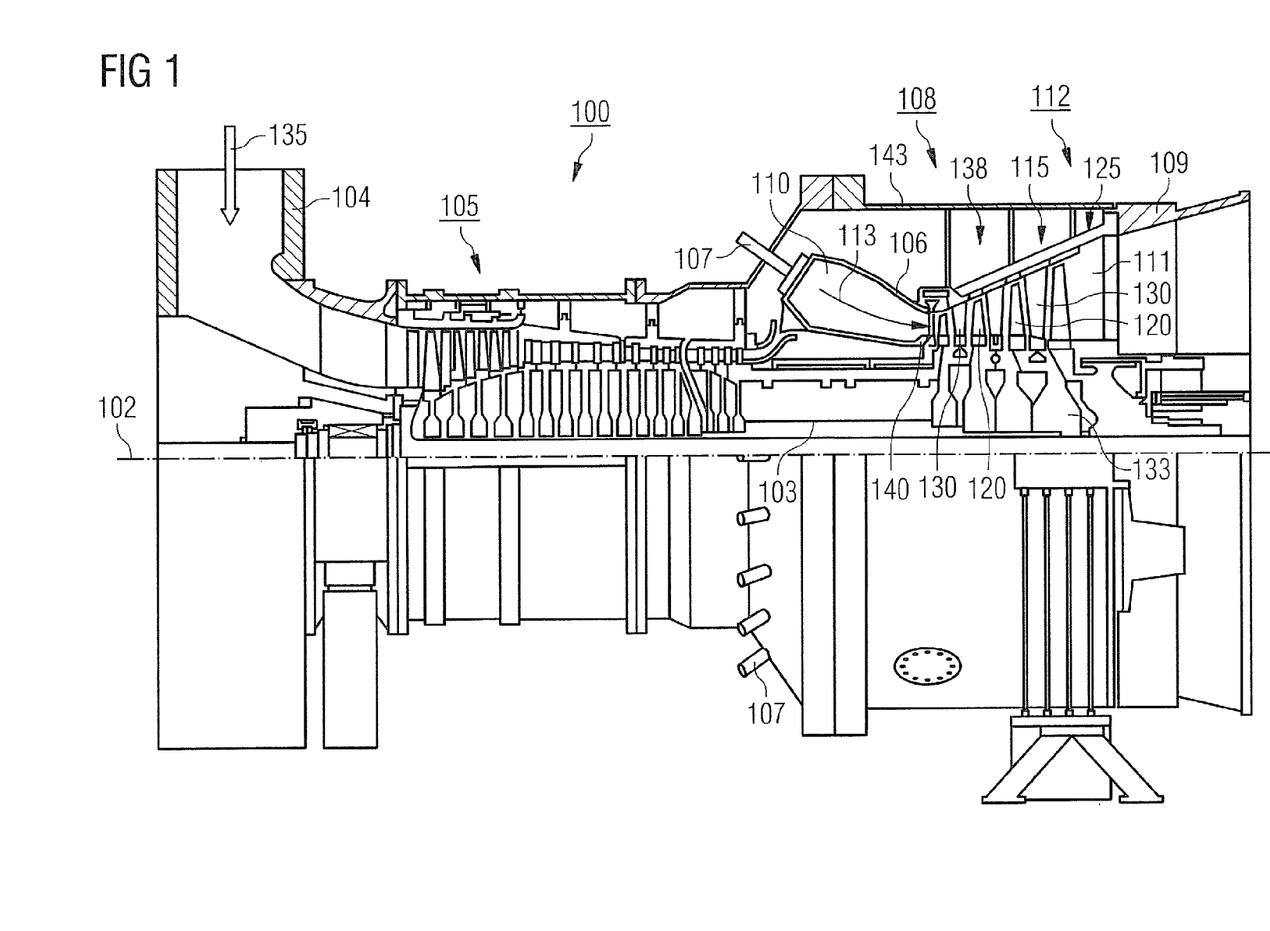
FIG. 1 shows a gas turbine by way of example in a partial longitudinal section.

FIG. 1 shows a gas turbine 100 by way of example in a partial longitudinal section.

The gas turbine 100 internally comprises a rotor 103, which will also be referred to as the turbine rotor, mounted so as to rotate about a rotation axis 102 and having a shaft 101.

Successively along the rotor 103, there are an intake manifold 104, a compressor 105, an e.g. toroidal combustion chamber 110, in particular a ring combustion chamber, having a plurality of burners 107 arranged coaxially, a turbine 108 and the exhaust manifold 109.

The ring combustion chamber 110 communicates with an e.g. annular hot gas channel 111. There, for example, four successively connected turbine stages 112 form the turbine 108.

Each turbine stage 112 is formed for example by two blade rings. As seen in the flow direction of a working medium 113, a guide vane row 115 is followed in the hot gas channel 111 by a row 125 formed by rotor blades 120.

The guide vanes 130 are fastened on an inner housing 138 of a stator 143 while the rotor blades 120 of a row 125 are fastened on the rotor 103, for example by means of a turbine disk 133.

Coupled to the rotor 103, there is a generator or a work engine (not shown).

During operation of the gas turbine 100, air 135 is taken in and compressed by the compressor 105 through the intake manifold 104. The compressed air provided at the turbine-side end of the compressor 105 is delivered to the burners 107 and mixed there with a fuel. The mixture is then burnt to form the working medium 113 in the combustion chamber 110. From there, the working medium 113 flows along the hot gas channel 111 past the guide vanes 130 and the rotor blades 120. At the rotor blades 120, the working medium 113 expands by imparting momentum, so that the rotor blades 120 drive the rotor 103 which drives the work engine coupled to it.

The components exposed to the hot working medium 113 become heated during operation of the gas turbine 100. Apart from the heat shield elements lining the ring combustion chamber 110, the guide vanes 130 and rotor blades 120 of the first turbine stage 112, as seen in the flow direction of the working medium 113, are heated the most.

In order to withstand the temperatures prevailing there, they may be cooled by means of a coolant.

Substrates of the components may likewise comprise a directional structure, i.e. they comprise a single crystal (SX structure) or only longitudinally directed grains (DS structure).

Iron-, nickel- or cobalt-based superalloys are for example used as material for the components, in particular for the turbine blades 120, 130 and components of the combustion chamber 110.

Such superalloys are known for example from EP 1 204 776 B1, EP 1 306 454, EP 1 319 729 A1, WO 99/67435 or WO 00/44949.

The blades 120, 130 may likewise have coatings against corrosion (MCrAlX; M is at least one element from the group iron (Fe), cobalt (Co), nickel (Ni), X is an active element and stands for yttrium (Y) and/or silicon, scandium (Sc) and/or at least one rare earth element, or hafnium). Such alloys are known from EP 0 486 489 B1, EP 0 786 017 B1, EP 0 412 397 B1 or EP 1 306 454 A1.

On the MCrAlX, there may furthermore be a thermal barrier coating which consists for example of $ZrO_2$, $Y_2O_3$—$ZrO_2$, i.e. it is not stabilized or is partially or fully stabilized by yttrium oxide and/or calcium oxide and/or magnesium oxide. Rod-shaped grains are produced in the thermal barrier coating by suitable coating methods, for example electron beam evaporation (EB-PVD).

The guide vane 130 comprises a guide vane root (not shown here) facing the inner housing 138 of the turbine 108, and a guide vane head lying opposite the guide vane root. The guide vane head faces the rotor 103 and is fixed on a fastening ring 140 of the stator 143.

Figure 2:
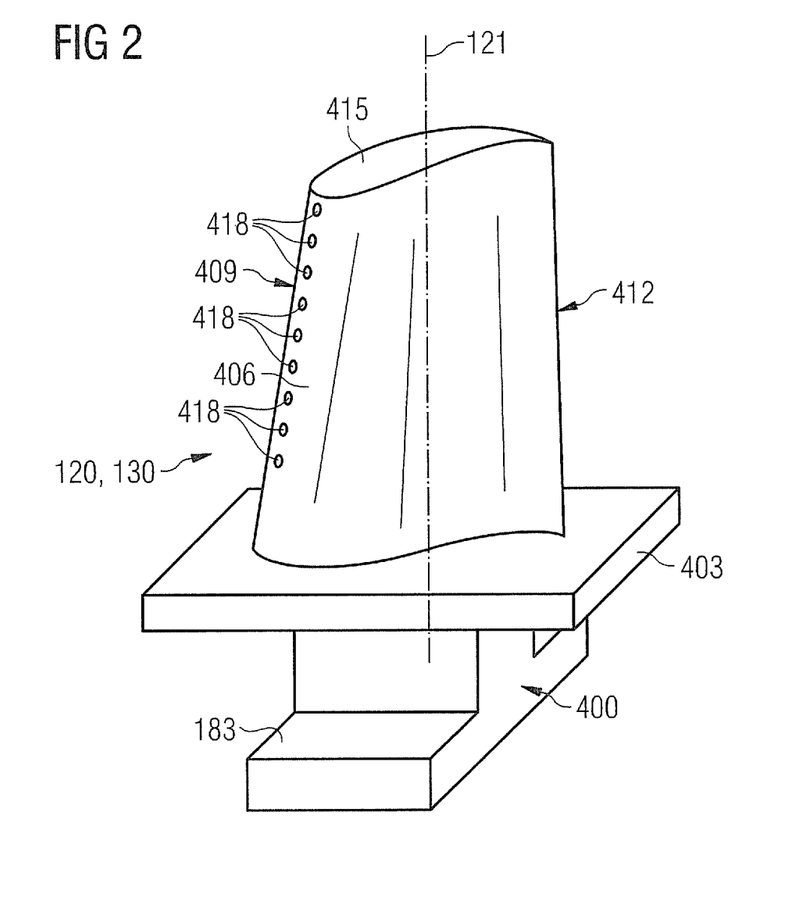
FIG. 2 shows a perspective view of a turbine blade.

FIG. 2 shows a perspective view of a rotor blade 120 or guide vane 130 of a turbomachine, which extends along a longitudinal axis 121.

The turbomachine may be a gas turbine of an aircraft or of a power plant for electricity generation, a steam turbine or a compressor.

The blade 120, 130 comprises, successively along the longitudinal axis 121, a fastening region 400, a blade platform 403 adjacent thereto as well as a blade surface 406 and a blade tip 415.

As a guide vane 130, the vane 130 may have a further platform (not shown) at its vane tip 415.

A blade root 183 which is used to fasten the rotor blades 120, 130 on a shaft or a disk (not shown) is formed in the fastening region 400.

The blade root 183 is configured, for example, as a hammerhead. Other configurations as a firtree or dovetail root are possible.

The blade 120, 130 comprises a leading edge 409 and a trailing edge 412 for a medium which flows past the blade surface 406.

In conventional blades 120, 130, for example solid metallic materials, in particular superalloys, are used in all regions 400, 403, 406 of the blade 120, 130.

Such superalloys are known for example from EP 1 204 776 B1, EP 1 306 454, EP 1 319 729 A1, WO 99/67435 or WO 00/44949.

The blade 120, 130 may in this case be manufactured by a casting method, also by means of directional solidification, by a forging method, by a machining method or combinations thereof.

Workpieces with a single-crystal structure or single-crystal structures are used as components for machines which are exposed to heavy mechanical, thermal and/or chemical stresses during operation.

Such single-crystal workpieces are manufactured, for example, by directional solidification from the melt. These are casting methods in which the liquid metal alloy is solidified to form a single-crystal structure, i.e. to form the single-crystal workpiece, or is directionally solidified.

Dendritic crystals are in this case aligned along the heat flux and form either a rod crystalline grain structure (columnar, i.e. grains which extend over the entire length of the workpiece and in this case, according to general terminology usage, are referred to as directionally solidified) or a single-crystal structure, i.e. the entire workpiece consists of a single crystal. It is necessary to avoid the transition to globulitic (polycrystalline) solidification in these methods, since non-directional growth will necessarily form transverse and longitudinal grain boundaries which negate the beneficial properties of the directionally solidified or single-crystal component.

When directionally solidified structures are referred to in general, this is intended to mean both single crystals which have no grain boundaries or at most small-angle grain boundaries, and also rod crystal structures which, although they do have grain boundaries extending in the longitudinal direction, do not have any transverse grain boundaries. These latter crystalline structures are also referred to as directionally solidified structures.

Such methods are known from U.S. Pat. No. 6,024,792 and EP 0 892 090 A1.

The blades 120, 130 may likewise have coatings against corrosion or oxidation, for example MCrAlX (M is at least one element from the group iron (Fe), cobalt (Co), nickel (Ni), X is an active element and stands for yttrium (Y) and/or silicon and/or at least one rare earth element, or hafnium (Hf)). Such alloys are known from EP 0 486 489 B1, EP 0 786 017 B1, EP 0 412 397 B1 or EP 1 306 454 A1.

The density is preferably 95% of the theoretical density.

A protective aluminum oxide layer (TGO=thermally grown oxide layer) is formed on the MCrAlX coating (as an interlayer or as the outermost coat).

The coating composition preferably comprises Co-30Ni-28Cr-8Al-0.6Y-0.7Si or Co-28Ni-24Cr-10Al-0.6Y. Besides these cobalt-based protective coatings, it is also preferable to use nickel-based protective coatings such as Ni-10Cr-12Al-0.6Y-3Re or Ni-12Co-21Cr-11Al-0.4Y-2Re or Ni-25Co-17Cr-10Al-0.4Y-1.5Re.

On the MCrAlX, there may furthermore be a thermal barrier coating, which is preferably the outermost coat and consists for example of $ZrO_2$, $Y_2O_3$—$ZrO_2$, i.e. it is not stabilized or is partially or fully stabilized by yttrium oxide and/or calcium oxide and/or magnesium oxide.

The thermal barrier coating covers the entire MCrAlX coating.

Rod-shaped grains are produced in the thermal barrier coating by suitable coating methods, for example electron beam evaporation (EB-PVD).

Other coating methods may be envisaged, for example atmospheric plasma spraying (APS), LPPS, VPS or CDV. The thermal barrier coating may comprise porous, micro- or macro-cracked grains for better thermal shock resistance. The thermal barrier coating is thus preferably more porous than the MCrAlX coating.

Refurbishment means that components 120, 130 may need to be stripped of protective coatings (for example by sandblasting) after their use. The corrosion and/or oxidation layers or products are then removed. Optionally, cracks in the component 120, 130 are also repaired. The component 120, 130 is then recoated and the component 120, 130 is used again.

The blade 120, 130 may be designed to be hollow or solid. If the blade 120, 130 is intended to be cooled, it will be hollow and optionally also comprise film cooling holes 418 (indicated by dashes).

Figure 3:
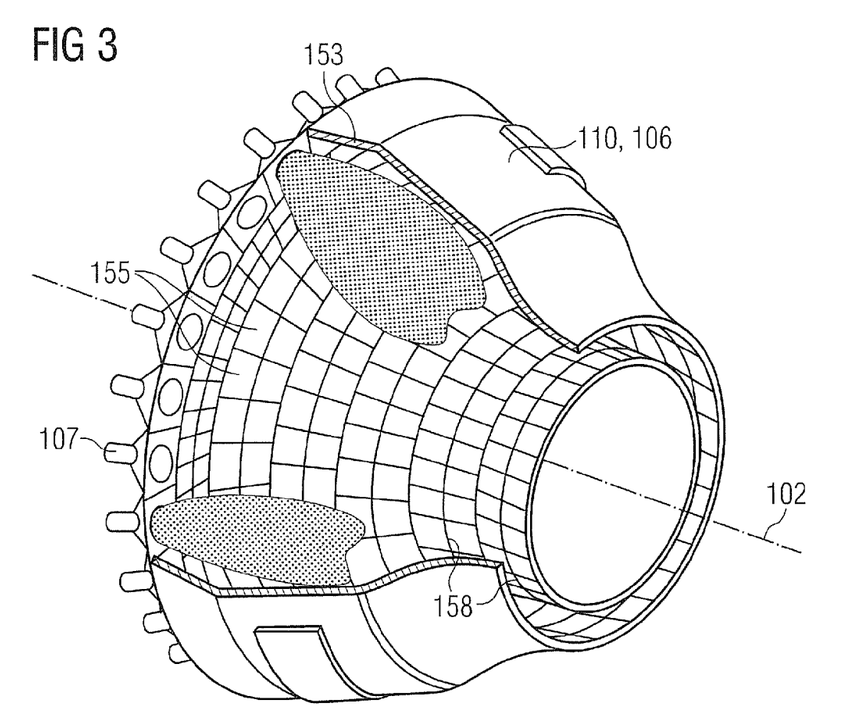
FIG. 3 shows an example of a gas turbine combustion chamber in a perspective representation.

FIG. 3 shows a combustion chamber 110 of a gas turbine. The combustion chamber 110 is designed for example as a so-called ring combustion chamber in which a multiplicity of burners 107, which produce flames 156 and are arranged in the circumferential direction around a rotation axis 102, open into a common combustion chamber space 154. To this end, the combustion chamber 110 as a whole is designed as an annular structure which is positioned around the rotation axis 102.

In order to achieve a comparatively high efficiency, the combustion chamber 110 is designed for a relatively high temperature of the working medium M, i.e. about 1000° C. to 1600° C. In order to permit a comparatively long operating time even under these operating parameters which are unfavorable for the materials, the combustion chamber wall 153 is provided with an inner lining formed by heat shield elements 155 on its side facing the working medium M.

Each heat shield element 155 made of an alloy is equipped with a particularly heat-resistant protective coating (MCrAlX coating and/or ceramic coating) on the working medium side, or is made of refractory material (solid ceramic blocks).

These protective coatings may be similar to the turbine blades, i.e. for example MCrAlX means: M is at least one element from the group iron (Fe), cobalt (Co), nickel (Ni), X is an active element and stands for yttrium (Y) and/or silicon and/or at least one rare earth element, or hafnium (Hf). Such alloys are known from EP 0 486 489 B1, EP 0 786 017 B1, EP 0 412 397 B1 or EP 1 306 454 A1.

On the MCrAlX, there may furthermore be an e.g. ceramic thermal barrier coating which consists for example of $ZrO_2$, $Y_2O_3$—$ZrO_2$, i.e. it is not stabilized or is partially or fully stabilized by yttrium oxide and/or calcium oxide and/or magnesium oxide.

Rod-shaped grains are produced in the thermal barrier coating by suitable coating methods, for example electron beam evaporation (EB-PVD).

Other coating methods may be envisaged, for example atmospheric plasma spraying (APS), LPPS, VPS or CDV. The thermal barrier coating may comprise porous, micro- or macro-cracked grains for better thermal shock resistance.

Refurbishment means that heat shield elements 155 may need to be stripped of protective coatings (for example by sandblasting) after their use. The corrosion and/or oxidation layers or products are then removed. Optionally, cracks in the heat shield element 155 are also repaired. The heat shield elements 155 are then recoated and the heat shield elements 155 are used again.

Owing to the high temperatures inside the combustion chamber 110, a cooling system may also be provided for the heat shield elements 155 or for their retaining elements. The heat shield elements 155 are then hollow, for example, and optionally also have cooling holes (not shown) opening into the combustion chamber space 154.

Figure 4:
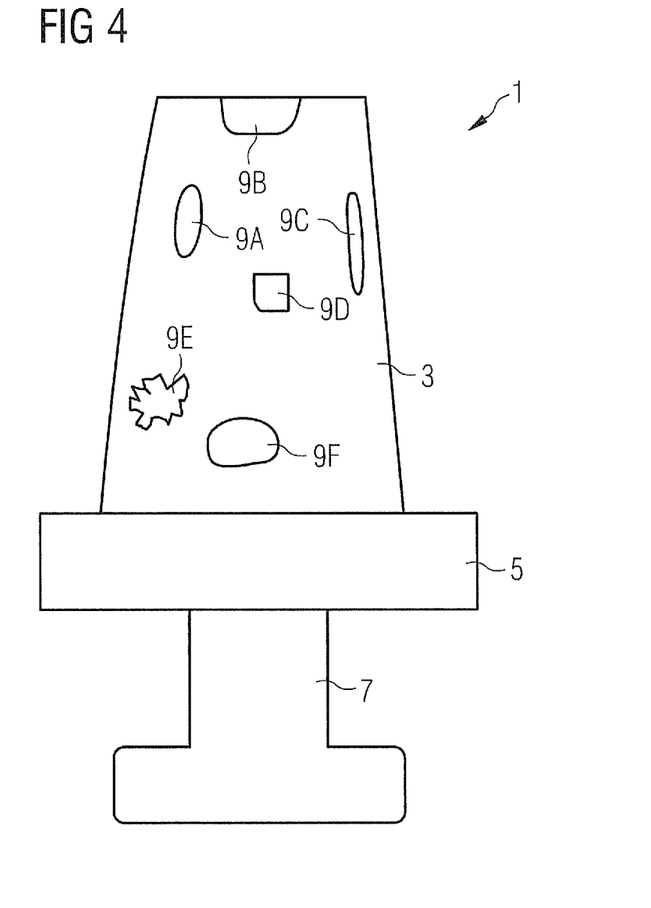
FIG. 4 shows a test component according to the invention configured as a turbine blade.

FIG. 4 shows a coated turbine blade 1 as an exemplary embodiment of a test component according to the invention. A coating system, which comprises a corrosion- and/or oxidation-inhibiting bond coat and a ceramic thermal barrier coating applied onto the bond coat, is provided as the coating. The coating system is in particular applied onto the blade surface 3, although it may also be applied on at least a part of the blade platform 5. The blade root 7 is generally not provided with such a coating system.

The coating system applied onto the blade surface 3 comprises a number of defined regions 9A to 9F, in which there are delaminations deliberately introduced into the coating system. The delaminations provided in the regions 9A to 9F are well defined particularly in respect of their position, their size, their shape and their signal intensities, which they generate in a thermography method.

Figure 5:
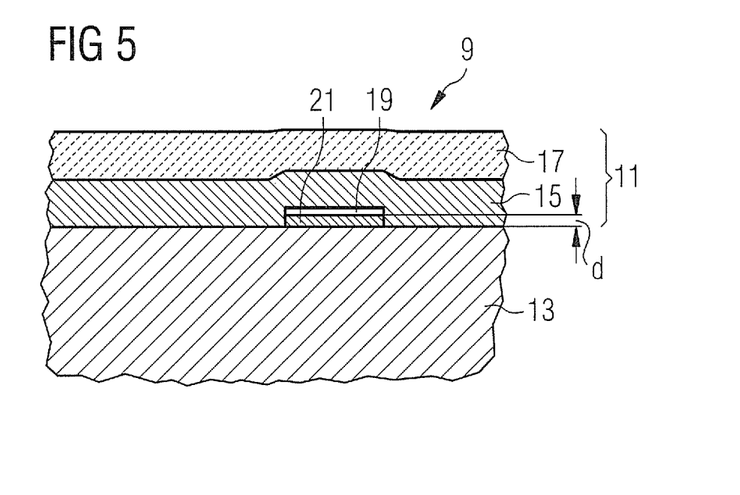
FIG. 5 shows the test component of FIG. 4 in a schematic sectional representation.

A schematic cross section through the blade surface 3 provided with the coating system is represented in FIG. 5. The cross section shows the substrate 13, as well as the coating system 11 applied thereon and comprising the bond coat 15 and the thermal barrier coating 17. A region 9 comprising a deliberately introduced delamination 19 is furthermore shown. In the region of the delamination 19, there is an auxiliary layer 21 which offers less adhesion for the coating system 11, in particular the bond coat 15, or a different thermal conductivity, than the substrate surface, i.e. the actual surface of the component.

In the present exemplary embodiment, the auxiliary layer is formed as a ceramic layer. It has a thickness d of at least 10 μm and preferably has a thickness in the range of between 10 μm and 100 μm, particularly in the range of between 30 and 40 μm. The conditions for the adhesion of the coating system on the auxiliary layer may be influenced by a plurality of factors, in particular by the roughness of the surface of the auxiliary layer 21; less roughness reduces the adhesion and therefore increases the delamination. However, the thickness of the auxiliary layer 21 also plays a role, with thicker auxiliary layers leading to lower adhesion and therefore more pronounced delaminations. Furthermore, the adhesion also depends on the material used for the auxiliary layer 21.

Besides a defined thickness and a defined surface roughness, the auxiliary layer 21 also has a defined shape and a defined size. The size and shape of the deliberately introduced delamination can thereby be established.

In a specific embodiment of the coating system 11 and the auxiliary layer 21, the bond coat 15 is formed as an MCrAlY layer and the thermal barrier coating 17 as a zirconium oxide layer at least partially stabilized with yttrium. A zirconium oxide layer at least partially stabilized with yttrium is likewise employed as the auxiliary layer 21. The MCrAlY layer adheres less well on its surface than on the surface of the nickel-, cobalt- or iron-based alloy of which the substrate consists in the present exemplary embodiment, so that the delamination 19 is formed at the position of the auxiliary layer 21 when the coating system 11 is applied.

Figure 6:
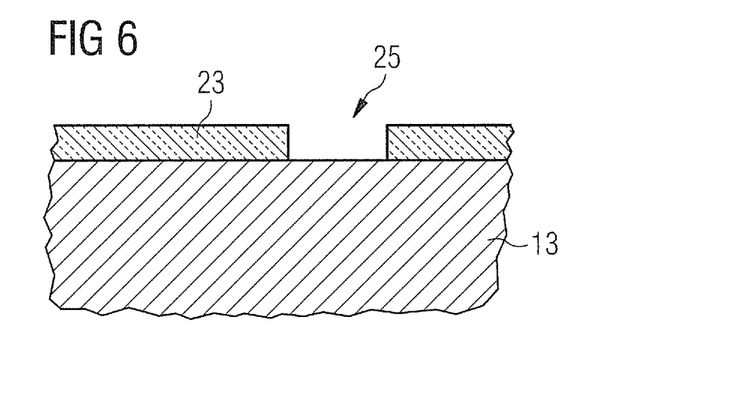
FIG. 6 shows the test component of FIG. 5 in a first stage of the production method.

The production of a test component, comprising regions in which there are deliberately introduced delaminations 19, will be described below with reference to FIGS. 6 to 9. At least one region which comprises a defined delamination of a coating system is produced by the method on the surface of a test component, which is represented in FIG. 6 by the substrate 13. To this end, in a first step, the uncoated substrate 13 is for example covered by means of a mask 23 so that a defined region 25 of the substrate surface remains uncovered. This uncovered region 25 corresponds after the end of the method to a region 9 comprising a deliberately introduced delamination.

Figure 7:
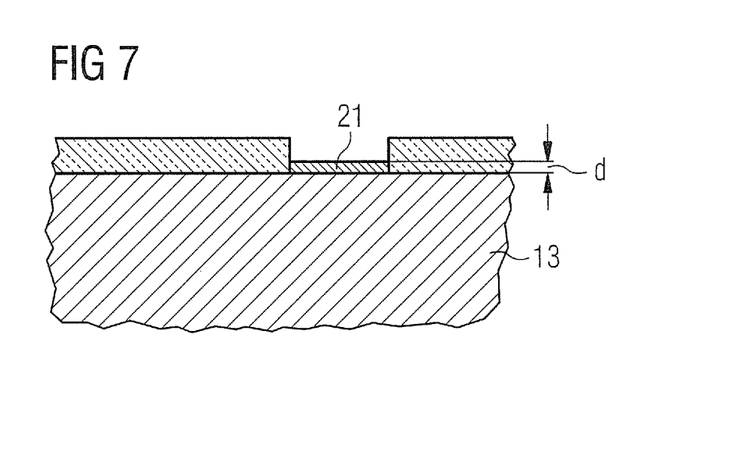
FIG. 7 shows the test component of FIG. 5 in a second stage of the production method.

After the substrate 13 has been covered, the uncovered region 25 is coated with the auxiliary layer 21, for example a zirconium oxide layer at least partially stabilized with yttrium. The auxiliary layer 21 may in this case be applied particularly by means of a thermal spraying method, for instance by means of atmospheric plasma spraying. By varying the spraying parameters, the surface roughness of the auxiliary layer 21 can in this case be influenced. The auxiliary layer 21 is applied until the desired layer thickness d is reached, which is at least 10 μm and in the present exemplary embodiment lies in the range of from 30 to 40 μm. The test component after application of the auxiliary layer 21 in the uncovered region 25 is represented in FIG. 7.

Figure 8:
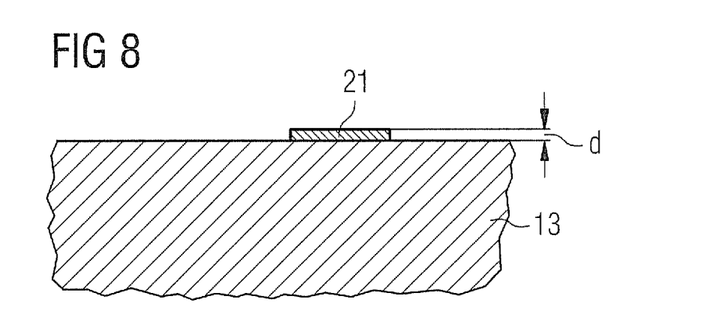
FIG. 8 shows the test component of FIG. 5 in a third stage of the production method.
Figure 9:
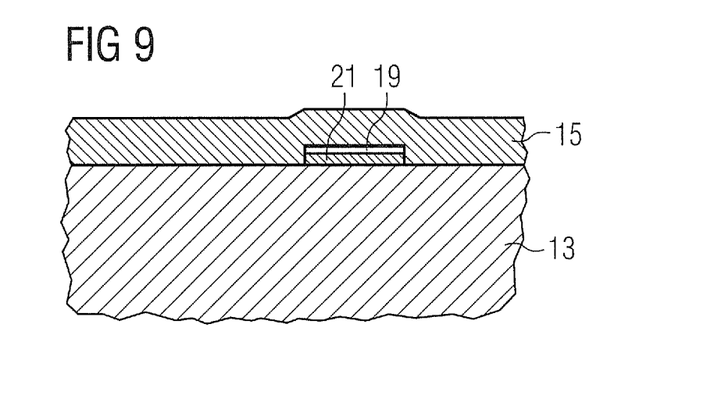
FIG. 9 shows the test component of FIG. 5 in a fourth stage of the production method.

After the auxiliary layer 21 has been applied, the covering 23 is removed so that the surface of the substrate is now uncovered outside the surface sections provided with the auxiliary layer 21. This state is represented in FIG. 8. The coating system 11 is then applied onto the substrate 13 which is in this state. In the present exemplary embodiment, the bond coat 15 is applied first, the adhesion of the bond coat on the auxiliary layer 21 being less than on the free substrate surface. A delamination 19 is therefore formed over the auxiliary layer 21, as shown schematically in FIG. 9. In the present exemplary embodiment, an MCrAlY layer is employed as the bond coat 15, which may be applied either by means of a thermal spraying method or by means of vapor deposition.

A thermal barrier coating 17 is subsequently deposited onto the substrate 13 provided with the bond coat 15. In the present exemplary embodiment, a zirconium oxide layer at least partially stabilized with yttrium oxide is employed as the thermal barrier coating 17. Like the application of the bond coat, the application of the ceramic thermal barrier coating may be carried out by means of a thermal spraying method or by means of vapor deposition. In particular, atmospheric plasma spraying may be envisaged as a thermal spraying method both for the deposition of the bond coat and for the deposition of the thermal barrier coating. After the ceramic thermal barrier coating has been applied, the final state of the test component as represented in FIG. 5 is reached.

The test component produced with the aid of the method according to the invention therefore comprises at least one delamination whose position on the test component, i.e. in the present exemplary embodiment on the turbine blade, is likewise previously known together with the size and shape of the delamination. Since the degree of adhesion of the coating system 11 on the auxiliary layer 21 can also be influenced during production of the test component, the delamination can also be produced in a controlled way with a view to the signal to the expected, which the delamination provides in a thermography method. Such a test component can then be used to test a thermography apparatus, designed for carrying out a thermography method, for its correct operation with a view to the detection of delaminations. In order to test the thermography apparatus for its correct operation, the test component is introduced into the thermography apparatus and the delaminations existing in the coating system are detected by means of the thermography method employed in the thermography apparatus. The properties of the delamination which are detected by means of the thermography method, i.e. its position, size and shape, and the degree of disbonding, can then be compared with the previously known properties of the existing delaminations existing in the test component and having been deliberately introduced. With the aid of the correspondence of the measured properties with the previously known properties, the quality of the detection by means of the thermography method can be deduced. Optionally, parameters of the thermography apparatus may be readjusted on the basis of the test results, in order to improve the detection accuracy.

With the aid of the invention as described with reference to exemplary embodiments, it is possible to produce test components which can advantageously be used in order to test thermography apparatuses. Furthermore, components which have dropped out of the production chain early on and therefore represent reject ware, which could no longer be used for anything else, can be used to produce the test components.

The invention claimed is:

1. A method for producing a test component having a metallic substrate that is to be coated with a coating system, the coating system including a bond coat and a thermal barrier coating, the method comprising:

applying a localized auxiliary layer directly on the metallic substrate, wherein the auxiliary layer is a first ceramic layer, applying the bond coat as a metallic layer after having applied the localized auxiliary layer, and applying the thermal barrier coating as a second ceramic layer over the metallic bond coat, wherein applying the localized auxiliary layer deliberately produces, on a surface of the test component, at least one region comprising a defined delamination of the coating system.

2. The method as claimed in claim 1, wherein the production of the defined delamination comprises:

covering an uncoated component, wherein at least one defined region of the surface of the component remains uncovered;

applying the auxiliary layer onto the at least one uncovered region of the surface, the auxiliary layer being selected so that the coating system has a lower adhesion or a different thermal conductivity compared with the surface of the component itself;

removing the covering; and coating the component with the coating system.

3. The method as claimed in claim 2, wherein the auxiliary layer is applied via a thermal spraying method.

4. The method as claimed in claim 2, wherein the auxiliary layer is applied via atmospheric plasma spraying.

5. The method as claimed in claim 2, wherein the auxiliary layer has a layer thickness of at least 10 µm.

6. The method as claimed in claim 1, wherein the auxiliary layer comprises a layer of zirconium oxide, which is at least partially stabilized with yttrium oxide.

7. A test component, comprising:

a metallic substrate, a localized auxiliary layer applied directly the metallic substrate, wherein the auxiliary layer comprises a first ceramic layer, and a coating system, comprising:

a bond coat comprising a metallic layer which is applied after having applied the localized auxiliary layer, and a thermal barrier coating comprising a second ceramic layer which is applied over the metallic bond coat, wherein a delamination is introduced into the coating system by way of the localized auxiliary layer, with defined properties in at least one defined region of the test component.

8. The test component as claimed in claim 7, wherein the auxiliary layer for the coating system has a lower adhesion or a different thermal conductivity relative to the surface of the component.

9. The test component as claimed in claim 7, wherein the auxiliary layer comprises a layer of zirconium oxide, which is at least partially stabilized with yttrium oxide.

10. The test component as claimed in claim 7, wherein the auxiliary layer has a layer thickness of at least 10 µm.

* * * * *